US007208447B2

(12) United States Patent
Geller et al.

(10) Patent No.: US 7,208,447 B2
(45) Date of Patent: Apr. 24, 2007

(54) POLYAMINO ACID-CATALYZED PROCESS FOR THE ENANTIOSELECTIVE EPOXIDATION OF α,β-UNSATURATED ENONES AND α,β-UNSATURATED SULFONES

(75) Inventors: Thomas Geller, Leverkusen (DE); Christa Maria Krüger, Münster (DE); Hans-Christian Militzer, Odenthal (DE)

(73) Assignee: Lanxess Deutschland GmbH, Leverkusen (DE)

( * ) Notice: Subject to any disclaimer, the term of this patent is extended or adjusted under 35 U.S.C. 154(b) by 412 days.

(21) Appl. No.: 10/926,458

(22) Filed: Aug. 25, 2004

(65) Prior Publication Data
US 2005/0027131 A1 Feb. 3, 2005

Related U.S. Application Data

(62) Division of application No. 10/202,600, filed on Jul. 24, 2002, now Pat. No. 6,822,053.

(30) Foreign Application Priority Data
Jul. 27, 2001 (DE) ................. 101 36 132

(51) Int. Cl.
B01J 20/26 (2006.01)
C07D 301/12 (2006.01)
C07D 303/32 (2006.01)
C08L 77/00 (2006.01)

(52) U.S. Cl. .............. 502/404; 525/430; 549/523; 549/531; 549/548

(58) Field of Classification Search .......... None
See application file for complete search history.

(56) References Cited

U.S. PATENT DOCUMENTS

| 6,225,482 B1 | 5/2001 | Drauz et al. ......... 549/525 |
| 6,409,769 B1 | 6/2002 | Shi ................... 649/519 |
| 6,700,004 B2 * | 3/2004 | Geller et al. ........ 549/524 |
| 6,770,766 B2 * | 8/2004 | Geller et al. ........ 549/531 |
| 2002/0133031 A1 | 9/2002 | Shi ................... 549/524 |

FOREIGN PATENT DOCUMENTS

| EP | 0 403 252 | 12/1990 |
| EP | 1 006 111 | 6/2000 |
| WO | 96/33183 | 10/1996 |

OTHER PUBLICATIONS

Bioorganic & Medicinal Chemistry, 7, (month unavailable) 1999, pp. 2145-2156, "Polyamino Acids as Catalysts in Asymmetric Synthesis" by M. J. Porter, S. M. Roberts, and J. Skidmore.
Tetrahedron Letters, 40, (month unavailable) 1999, pp. 5421-5424, "PaaSicats: Powerful Catalysts for Asymmetric Epoxidation of Enones. Novel Syntheses of α-Arylpropanoic Acids including (S)-Fenoprofen" by L. Carde, H. Davies, T. P. Geller and S. M. Roberts.
Tetrahedron Letters, 39, (month unavailable) 1998, pp. 7353-7356, "Water vs. Desiccant. Improvement of Yb-BINOL Complex Catalyzed Enantioselective Epoxidation of Enones" by S. Watanabe, Y. Kobayashi, T. Arai, H. Sasai, M. Bougauchi, and M. Shibasaki.
Tetrahedron Letters, 39, (month unavailable) 1998, pp. 1599-1602, "Asymmetric Phase-Transfer Mediated Epoxidation of α, β-Unsaturated Ketones Using Catalysts Derived From *Cinchona* Alkaloids" by B. Lygo and P. G. Wainwright.
Tetrahedron Letters, No. 21, pp. 1831-1834, (month unavailable) 1976, "Catalytic Asymmetric Induction in Oxidation Reactions. The Synthesis of Optically Active Epoxides," by R. Helder, J. C. Hummelen, R. W. P. Laane, J. S. Wiering and H. Wynberg.
Tetrahedron Letters, 39, (month unavailable) 1998, pp. 7563-7566, "Asymmetric Epoxidation of α, β-Unsaturated Ketones Under Phase-Transfer Catalyzed Conditions" by S. Arai, H. Tsuge and T. Shioiri.
Tetrahedron Letters, 39, (month unavailable) 1998, pp. 7321-7322, "Remarkable Ligand Effect on the Enantioselectivity of the Chiral Lanthanum Complex-Catalyzed Asymmetric Epoxidation of Enones" by K. Daikai, M. Kamaura, and J. Inanaga.
Angew. Chem. Int. Ed. Engl., (month unavailable) 1997, 36, No. 4, pp. 410-412, "Asymmetric Epoxidation of Chalcones with Chirally Modified Lithium and Magnesium *tert*-Butyl Peroxides" by C. L. Elston, R. F. W. Jackson, S. J. F. MacDonald and P. J. Murray.
Liebigs Ann./Recueil, (month unavailable) 1997, pp. 1101-1113, "Zinc-Mediated Asymmetric Epoxidation of α-Enones" by, D. Enders, J. Zhu, and L. Kramps.
Tetrahedron Letters 40, (month unavailable) 1999, pp. 5207-5210, "*cis*-Selective Aziridination of *cis*- or *trans* -α, β-Unsaturated Amides Using Diaziridine" by K. Hori, H. Sugihara, Y. N. Ito and T. Katsuki.
J. Chem. Soc., Perkin Trans. I, (month unavailable) 1982, pp. 1317-1324, "Synthetic Enzymes. Part 2.[1] Catalytic Asymmetric Epoxidation by means of Polyamino-acids in a Triphase System" by S. Juliá, J. Guixer, J. Masana and J. Rocas.
Org. Synth. Mod. Trends. Proc. 1UPAC Symp., 6th, (month unavailable) 1986, pp. 275-284, "Asymmetric syntheses catalyzed by natural and synthetic peptides" by S. Colonna, A. Manfredi and M. Spadoni.
J. Chem. Soc. Perkin Trans. 1, (month unavailable) 1995, pp. 1467-1468, "Enantiocomplementary asymmetric epoxidation of selected enones using poly-L-leucine and poly-D-leucine" by M. E. L. Sánchez and S. M. Roberts.

(Continued)

*Primary Examiner*—Robert Sellers
(74) *Attorney, Agent, or Firm*—Michael A. Miller

(57) ABSTRACT

The invention relates to a novel process that makes it possible to epoxidize α,β-unsaturated enones or α,β-unsaturated sulfones with high conversions and enantiomeric excesses in a two-phase system without addition of water in the presence of an organic solvent, a base, an oxidant, a diastereomer- and enantiomer-enriched homo-polyamino acid that has not been separately preactivated as catalyst, and a specific phase-transfer catalyst as cocatalyst.

2 Claims, No Drawings

OTHER PUBLICATIONS

J. Chem. Soc., Perkin Trans. 1, (month unavailble) 1997, pp. 3501-3507, "Improved procedure for Juliá-Colonna asymmetric epoxidation of α, β-unsaturated ketones: total synthesis of diltiazem and Taxol™ side-chain" by B. M. Adger et al.

Tetrahedron Letters, 42, (month unavailable) 2001, pp. 3741-3743, "Asymmetric epoxidation of a geminally-disubstituted and some trisubstituted enones catalysed by poly-L-leucine" by P. A. Bentley, J. F. Bickley, S. M. Roberts and A. Steiner.

Chem. Commun., (month unavailable) 1997, pp. 739-740, "Asymmetric epoxidation of enones employing polymeric α-amino acids in non-aqueous media" P. A. Bentley et al.

Chirality 9: pp. 198-202, (month unavailable) 1997, "Preparation of Polyamino Acid Catalysts for Use in Juliá Asymmetric Epoxidation" by P. A. Bentley et al.

Chem. Commun., (month unavailable) 1998, pp. 1159-1160, "New procedures for the Juliá-Colonna asymmetric epoxidation: synthesis of ( +)-clausenamide" by M. W. Cappi et al.

Tetrahedron: Asymmetry, vol. 8, No. 19, pp. 3163-3173, (month unavailable) 1997, Synthetic applications of polymeric α-amino acids by S. Ebrahim and M. Wills.

J. Org. Chem., (month unavailable) 1993, 58, pp. 6247-6254, "A Practical, Enantioselective Synthesis of SK&F 104353" by J. R. Flisak et al.

Angew. Chem. Int. Ed. Engl. 19, (month unavailable) 1980, No. 11, "Synthetic Enzymes", Highly Stereoselective Epoxidation of Chalcone in a Triphasic Toluene-Water-Poly[(S)-alanine] System by S. Juliá, J. Masana, and J. C. Vega.

Tetrahedron Letters, 39, (month unavailable) 1998, pp. 9297-9300, "Towards a Mechanistic Insight into the Juliá-Colonna Asymmetric Epoxidation of α, β-Unsaturated Ketones Using Discrete Lengths of Poly-leucine." by P. A. Bentley et al.

Baures P. W. et al: "An efficient asymmetric synthesis of substituted phenyl glycidic esters" Tetrahedron Letters., Bd. 31, Nr. 45, 1990, Seiten 6501-6504, XP002006755, Elsevier Science Publishers, Amsterdam., NL ISSN: 0040-4039 das ganze Dokument.

Dhanda, Anupma et al: "PaaSiCats: Novel polyamino acid catalysts" Chirality (2000), 12(5/6), 313-317, XP008009815, das ganze Dokument.

Flood R. W. et al: "Efficient asymmetric epoxidation of alpha, beta-unsaturated ketones using a soluble triblock polyethyleneglycol-polyamino acid catalyst" Organic Letters., Bd. 3, Nr. 5, Mar. 8, 2001, Seiten 683-686, XP002219131 ACS, Washington, DC., US ISSN: 1523-7060 das ganze Dokument.

\* cited by examiner

POLYAMINO ACID-CATALYZED PROCESS FOR THE ENANTIOSELECTIVE EPOXIDATION OF α,β-UNSATURATED ENONES AND α,β-UNSATURATED SULFONES

This application is a Divisional of Ser. No. 10/202,600, filed Jul. 24, 2002, U.S. Pat. No. 6,822,053.

BACKGROUND OF THE INVENTION

The invention relates to a novel polyamino acid-catalyzed process for the enantioselective epoxidation of α,β-unsaturated enones and α,β-unsaturated sulfones under two-phase conditions in the presence of specific cocatalysts.

Chiral, nonracemic epoxides are known as valuable synthons for preparing optically active drugs and materials (for example (a) Bioorg. Med. Chem., 1999, 7, 2145–2156; and (b) Tetrahedron Lett., 1999, 40, 5421–5424). These epoxides can be prepared by enantioselective epoxidation of double bonds. In this case, two stereocenters are produced in one synthetic step. It is therefore not surprising that a large number of methods have been developed for the enantioselective epoxidation of double bonds. However, there is still a great need for novel, improved methods for enantioselective epoxidation.

The epoxidation methods limited to the specific substrates in each case include methods for the enantioselective epoxidation of α,β-unsaturated enones.

Thus, for example, the use of chiral, nonracemic alkaloid-based phase-transfer catalysts for the epoxidation of enones is described in Tetrahedron Lett., 1998, 39, 7563–7566, Tetrahedron Lett., 1998, 39, 1599–1602, and Tetrahedron Lett., 1976, 21, 1831–1834.

Tetrahedron Lett., 1998, 39, 7353–7356, Tetrahedron Lett., 1998, 39, 7321–7322, and Angew. Chem., Int. Ed. Engl., 1997, 36, 410–412 furthermore describe possibilities for the metal-catalyzed asymmetric epoxidation of enones using organic hydroperoxides.

WO-A 99/52886 further describes the possibility of enantioselective epoxidation of enones in the presence of catalysts based on sugars. Another method for epoxidation using Zn organyls and oxygen in the presence of an ephedrine derivative has been published in Liebigs Ann./Recueil, 1997, 1101–1113.

Angew. Chem., Int. Ed. Engl., 1980, 19, 929–930, Tetrahedron, 1984, 40, 5207–5211, and J. Chem. Soc. Perkin Trans. 1, 1982, 1317–24 describe what is known as the classical three-phase Juliá epoxidation method. In this method, the enantioselective epoxidation of α,β-unsaturated enones is carried out with the addition of enantiomer- and diastereomer-enriched polyamino acids in the presence of aqueous hydrogen peroxide and NaOH solution and of an aromatic or halogenated hydrocarbon as solvent. Further developments of these so-called three-phase conditions are to be found in Org. Synth.; Mod. Trends, Proc. IUPAC Symp. 6th., 1986, 275. The method is now generally referred to as the Juliá-Colonna epoxidation.

According to EP-A 403,252, it is possible also to employ aliphatic hydrocarbons advantageously in this Juliá-Colonna epoxidation in place of the original solvents.

According to WO-A 96/33183 it is furthermore possible in the presence of the phase-transfer catalyst Aliquat® 336 ($[(CH_3)(C_8H_{17})_3N^+]Cl^-$) and using at the same time sodium perborate, which is of low solubility in water, instead of hydrogen peroxide, for the required amount of base (NaOH) to be reduced, compared with the original conditions of Juliá and Colonna (Tetrahedron, 1984, 40, 5207–5211), from about 3.7 to 1 equivalent.

Despite these improvements, the three-phase conditions have distinct disadvantages. The reaction times under the original conditions are in the region of days even for reactive substrates. For example, 1–6 days are required for trans-chalcone, depending on the polyamino acid used (Tetrahedron, 1984, 40, 5207–5211). A preactivation of the polyamino acid carried out in the reaction vessel, by stirring in the solvent with the addition of NaOH solution for 12 to 48 hours, shortens the reaction time for many substrates to 1 to 3 days. In this case, no intermediate workup of the catalyst is necessary (EP-A 403,252). The preactivation can be reduced to a minimum of 6 h in the presence of the NaOH/hydrogen peroxide system (J. Chem. Soc. Perkin Trans. 1, 1995, 1467–1468).

Despite this improvement, the three-phase method cannot be applied to substrates which are sensitive to hydroxide ions (J. Chem. Soc., Perkin Trans. 1, 1997, 3501–3507). A further disadvantage of these classical conditions is that the polyamino acid forms a gel during the reaction (or even during the preactivation). This restricts the required mixing during the reaction and impedes the working up of the reaction mixture.

Tetrahedron Lett., 2001, 42, 3741–43 discloses that under the three-phase conditions the addition of the phase-transfer catalyst (PTC) Aliquat 336 in the epoxidation of phenyl-E-styryl sulfone leads to only a slow reaction rate (reaction time: 4 days) and a poor enantiomeric excess (21% ee). To date, no example of the use of PTCs for the epoxidation of α,β-unsaturated enones under the classical three-phase Juliá-Colonna conditions has been disclosed.

The Juliá-Colonna epoxidation has been improved further by a change in the reaction procedure. According to Chem. Commun., 1997, 739–740, (pseudo)-anhydrous reaction conditions can be implemented by using THF, 1,2-dimethoxyethane, tert-butyl methyl ether, or ethyl acetate as solvent, a non-nucleophilic base (for example, DBU), and a urea/hydrogen peroxide complex as oxidant. The epoxidation takes place distinctly more quickly under these so-called two-phase reaction conditions. According to J. Chem. Soc., Perkin Trans. 1, 1997, 3501–3507, therefore, the enantioselective epoxidation of hydroxide-sensitive enones under the Juliá-Colonna conditions is also possible for the first time in this way.

However, the observation that, on use of the two-phase conditions, the polyamino acid must be preactivated in a separate process in order to achieve rapid reaction times and high enantiomeric excesses proves to be a distinct disadvantage. Several days are needed for this preactivation, which takes place by stirring the polyamino acid in a toluene/NaOH solution. According to Tetrahedron Lett., 1998, 39, 9297–9300, the required preactivated catalyst is then obtained after a washing and drying procedure. However, the polyamino acid activated in this way forms a paste under the two-phase conditions, which impedes mixing during the reaction and the subsequent workup. According to EP-A 1,006,127, this problem can be solved by adsorbing the activated polyamino acid onto a solid support. Polyamino acids supported on silica gel are referred to as SCAT (silica adsorbed catalysts).

According to EP-A 1,006,111, a further variant of the Juliá-Colonna epoxidation is catalysis of the enantioselective epoxidation by the activated polyamino acid in the presence of water, a water-miscible solvent (for example, 1,2-dimethoxyethane), and sodium percarbonate. However, the use of water-miscible solvents complicates the workup (extraction) in this process.

In the Juliá-Colonna epoxidation, the reaction rate and the enantiomeric excess (ee) that can be achieved depend greatly on the polyamino acid used and the mode of preparation thereof (*Chirality*, 1997, 9, 198–202). In order to obtain approximately comparable results, a standard system with poly-L-leucine (pII) as catalyst and trans-chalcone as precursor is used throughout for the development and description of novel methods in the literature. However, besides D- or L-polyleucine, other polyamino acids such as, for example D- or L-neopentylglycine are also used successfully (EP-A 1,006,127).

The object of the present invention was to provide a process that makes the homo-polyamino acid-catalyzed enantioselective epoxidation of α,β-unsaturated enones and α,β-unsaturated sulfones possible but is not subject to the disadvantages of the above-described variants of the Juliá-Colonna epoxidation. It was intended in particular to find a rapid and broadly applicable method that avoids the separate, time-consuming and complicated preactivation of the polyamino acid. At the same time, it was intended that the process have advantages in relation to the space/time yield, handling, economics, and ecology on the industrial scale.

It has now been found, surprisingly, that the epoxidation of α,β-unsaturated enones and α,β-unsaturated sulfones can be carried out under two-phase conditions in the presence of a polyamino acid, as catalyst, that has not been subjected to previous separate activation when the epoxidation takes place in the presence of a phase-transfer catalyst. This procedure surprisingly makes it possible for the reaction times to be very short with, at the same time, high enantiomeric excesses.

SUMMARY OF THE INVENTION

The invention thus relates to a process for the epoxidation of α,β-unsaturated enones or α,β-unsaturated sulfones in the presence of
(1) an organic solvent,
(2) a base,
(3) an oxidant,
(4) a diastereomer- and enantiomer-enriched homo-polyamino acid as catalyst that has not been separately preactivated, and
(5) a phase-transfer catalyst,
but without addition of water.

DETAILED DESCRIPTION OF THE INVENTION

It is crucial that the process according to the invention be carried out in the presence of a phase-transfer catalyst. Examples that can be used are quaternary ammonium salts, quaternary phosphonium salts, onium compounds, or pyridinium salts.

Phase-transfer catalysts that have proved particularly suitable are quaternary ammonium or phosphonium salts of the general formula (I)

$(R^1R^2R^3R^4A)^+X^-$ (I)

in which
A is N or P,
$X^-$ is an inorganic or organic anion, $R^1$ and $R^2$ are identical or different and are alkyl, aryl, aralkyl, cycloalkyl, or heteroaryl radicals that are optionally substituted by one or more identical or different halogen radicals, and
$R^3$ and $R^4$ are identical or different and are alkyl, aryl, aralkyl, cycloalkyl, or heteroaryl radicals that are optionally substituted by one or more identical or different halogen radicals, or $R^3$ and $R^4$ together form a $C_4$–$C_6$-cycloalkyl ring with A.

Phase-transfer catalysts of the general formula (I) that have proved suitable are those in which A and $X^-$ have the above-mentioned meanings, and $R^1$, $R^2$, $R^3$, and $R^4$ are identical or different and are $C_1$–$C_{18}$-alkyl, $C_6$–$C_{18}$-aryl, $C_7$–$C_{19}$-aralkyl, $C_5$–$C_7$-cycloalkyl, or $C_3$–$C_{18}$-heteroaryl.

Particularly suitable phase-transfer catalysts are $((C_4H_9)_4N)^+Hal^-$ (particularly $((C_4H_9)_4N)^+Br^-$), $((C_4H_9)_4P)^+Hal^-$ (particularly $((C_4H_9)_4N)^+Br^-$), $((C_4H_9)_4N)^+HSO_4^-$, $((C_8H_{17})_4N)^+Br^-$, $[(CH_3)(C_8H_{17})_3N^+]Cl^-$, and $[(CH_3)(C_4H_9)_3N^+]Cl^-$.

$X^-$ in the general formula (I) is an inorganic or organic cation, preferably $F^-$, $Cl^-$, $Br^-$, $I^-$, $OH^-$, $HSO_4^-$, $SO_4^-$, $NO_3^-$, $C_2H_5COO^-$, $C_3H_7COO^-$, $CF_3SO_3^-$, or $C_4F_9SO_3^-$.

The phase-transfer catalysts to be employed according to the invention are normally commercially available or else can be prepared by methods familiar to the skilled person.

The amount of added phase-transfer catalyst is not critical and is normally in the range 0.1 to 20 mol % (preferably in the range 0.5 to 15 mol %, particularly preferably in the range 0.5 to 11 mol %), in each case based on the α,β-unsaturated enones or α,β-unsaturated sulfone employed. However, it is to be observed with amounts that are even lower than 0.1 mol % that the reaction rate decreases markedly, while the high enantiomeric excess is unchanged.

It is possible to employ as α,β-unsaturated enones or α,β-unsaturated sulfones the compounds of the general formula (II)

(II)

in which
X is (C=O) or (SO₂), and
$R^5$ and $R^6$ are identical or different and are $(C_1$–$C_{18})$-alkyl, $(C_2$–$C_{18})$-alkenyl, $(C_2$–$C_{18})$-alkynyl, $(C_3$–$C_8)$-cycloalkyl, $(C_6$–$C_{18})$-aryl, $(C_7$–$C_{19})$-aralkyl, $(C_1$–$C_{18})$-heteroaryl or $(C_2$–$C_{19})$-heteroaralkyl, each of which radicals is optionally substituted once or more than once by identical or different radicals $R^7$, halogen, $NO_2$, $NR^7R^8$, $PO_{0-3}R^7R^8$, $SO_{0-3}R^7$, $OR^7$, $CO_2R^7$, $CONHR^7$, or $COR^7$, and where optionally one or more $CH_2$ groups in the radicals $R^5$ and $R^6$ are replaced by O, $SO_{0-2}$, $NR^7$, or $PO_{0-2}R^7$,
where $R^7$ and $R^8$ are identical or different and are H, $(C_1$–$C_{18})$-alkyl, $(C_2$–$C_{18})$-alkenyl, $(C_2$–$C_{18})$-alkynyl, $(C_3$–$C_8)$-cycloalkyl, $(C_6$–$C_{18})$-aryl, $(C_1$–$C_{18})$-heteroaryl, $(C_1$–$C_8)$-alkyl-$(C_6$–$C_8)$-aryl, $(C_1$–$C_8)$-alkyl-$(C_1$–$C_{19})$-heteroaryl, or $(C_1$–$C_8)$-alkyl-$(C_3$–$C_8)$-cycloalkyl, each of which radicals $R^7$ and $R^8$ is optionally substituted once or more than once by identical or different halogen radicals.

A $(C_1$–$C_{18})$-alkyl radical means for the purpose of the invention a radical that has 1 to 18 saturated carbon atoms and that may have branches anywhere. It is possible to include in this group in particular the radicals methyl, ethyl, n-propyl, isopropyl, n-butyl, isobutyl, sec-butyl, tert-butyl, pentyl, and hexyl.

A $(C_2$–$C_{18})$-alkenyl radical has the features mentioned for the $(C_1$–$C_{18})$-alkyl radical, with the necessity for at least one carbon-carbon double bond to be present within the radical.

A $(C_2$–$C_{18})$-alkynyl radical has the features mentioned for the $(C_1$–$C_{18})$-alkyl radical, with the necessity for at least one carbon-carbon triple bond to be present within the radical.

A $(C_3$–$C_8)$-cycloalkyl radical means a cyclic alkyl radical having 3 to 8 carbon atoms and, where appropriate, a branch anywhere. Included are, particularly, radicals such as cyclopropyl, cyclobutyl, cyclopentyl, cyclohexyl, and cycloheptyl. One or more double bonds may be present in this radical.

A $(C_6$–$C_{18})$-aryl radical means an aromatic radical having 6 to 18 carbon atoms. Included are, particularly, radicals such as phenyl, naphthyl, anthryl, and phenanthryl.

A $(C_7$–$C_{19})$-aralkyl radical means a $(C_6$–$C_{18})$-aryl radical linked via a $(C_1$–$C_8)$-alkyl radical to the molecule.

A $(C_1$–$C_{18})$-heteroaryl radical designates for the purpose of the invention a five-, six-, or seven-membered aromatic ring system that has 1 to 18 carbon atoms and that has one or more heteroatoms (preferably N, O, or S) in the ring. These heteroaryl radicals include, for example, 2- or 3-furyl, 1-, 2-, and 3-pyrrolyl, 2- and 3-thienyl, 2-, 3-, and 4-pyridyl, 2-, 3-, 4-, 5-, 6-, and 7-indolyl, 3-, 4-, and 5-pyrazolyl, 2-, 4-, and 5-imidazolyl, 1-, 3-, 4-, and 5-triazolyl, 1-, 4-, and 5-tetrazolyl, acridinyl, quinolinyl, phenanthridinyl, 2-, 4-, 5-, and 6-pyrimidinyl, and 4-, 5-, 6-, and 7-(1-aza)-indolizinyl.

A $(C_2$–$C_{19})$-heteroaralkyl radical means a heteroaromatic system corresponding to the $(C_7$–$C_{19})$-aralkyl radical.

Halogen or Hal means in the context of this invention fluorine, chlorine, bromine, and iodine.

The substrates preferably employed in the process according to the invention are preferably α,β-unsaturated enones or α,β-unsaturated sulfones of the general formula (II) in which $R^5$ and $R^6$ are identical or different and are $(C_1$–$C_{12})$-alkyl, $(C_2$–$C_{12})$-alkenyl, $(C_2$–$C_{12})$-alkynyl, $(C_5$–$C_8)$-cycloalkyl, $(C_6$–$C_{12})$-aryl, or $(C_1$–$C_{12})$-heteroaryl, each of which radicals is optionally substituted once or more than once by identical or different radicals $R^7$, halogen, $NO_2$, $NR^7R^8$, $PO_{0-3}R^7R^8$, or $OR^7$, and $R^7$ and $R^8$ have the meanings indicated above for the general formula (II).

Substrates particularly preferably employed in the process according to the invention are α,β-unsaturated enones or α,β-unsaturated sulfones of the general formula (II) in which $R^5$ and $R^6$ are identical or different and are $(C_1$–$C_{12})$-alkyl, $(C_2$–$C_{12})$-alkenyl, $(C_2$–$C_{12})$-alkynyl, $(C_5$–$C_8)$-cycloalkyl, $(C_6$–$C_{12})$-aryl, or $(C_1$–$C_{12})$-heteroaryl, each of which radicals is optionally substituted once or more than once by identical or different radicals $R^7$, halogen, $NO_2$, $NR^7R^8$, $PO_{0-3}R^7R^8$, or $OR^7$, and $R^7$ and $R^8$ have the meanings indicated above for the general formula (II), with the proviso that at least one of the radicals $R^5$ or $R^6$ is a $(C_2$–$C_{12})$-alkenyl, $(C_2$–$C_{12})$-alkynyl, $(C_6$–$C_{12})$-aryl-, or $(C_1$–$C_{12})$-heteroaryl radical.

It is particularly preferred to subject substrates of the general formula (III) to the epoxidation according to the invention:

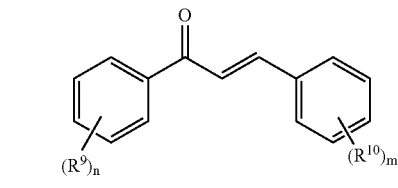

where
n and m are identical or different and are the numbers 0, 1, 2 or 3,
$R^9$ and $R^{10}$ are identical or different and are $NR^7R^8$, $NO_2$, $OR^7$, $(C_1$–$C_{12})$-alkyl, $(C_2$–$C_{12})$-alkenyl, $(C_2$–$C_{12})$-alkynyl, $(C_5$–$C_8)$-cycloalkyl, $(C_6$–$C_{12})$-aryl, or $(C_1$–$C_{12})$-heteroaryl, each of which radicals $R^9$ and $R^{10}$ is optionally substituted once or more than once by identical or different halogen radicals, and
$R^7$ and $R^8$ have the meanings mentioned previously for formula (II).

A decisive advantage of the process according to the invention is the fact that homo-polyamino acids that are not preactivated separately are employed as catalysts.

It is possible to use for the process according to the invention a wide variety of diastereomer- and enantiomer-enriched homo-polyamino acids. Preference is given, however, to the use of homo-polyamino acids selected from the group consisting of polyneopentylglycine, polyleucine, polyisoleucine, polyvaline, polyalanine, and polyphenylalanine. The most preferred from this group are polyneopentylglycine and polyleucine.

The chain length of the polyamino acids will be chosen so that, on the one hand, the chiral induction in the reaction is not impaired and, on the other hand, the costs of synthesizing the polyamino acids are not too great. The chain length of the homo-polyamino acids is preferably between 5 and 100 (preferably 7 to 50) amino acids. A chain length of 10 to 40 amino acids is very particularly preferred.

The homo-polyamino acids can be prepared by state of the art methods (*J. Org. Chem.*, 1993, 58, 6247 and *Chirality*, 1997, 9, 198–202). The method is to be applied to both optical antipodes of the amino acids. The use of a particular antipode of a polyamino acid correlates with the stereochemistry of the epoxide. That is to say, a poly-L-amino acid leads to the optical antipode of the epoxide that is obtained with a poly-D-amino acid.

The homo-polyamino acids can be either employed as such unchanged in the epoxidation or previously crosslinked with polyfunctional amines or chain-extended by other organic polymers. The crosslinking amines advantageously employed for a crosslinking are diaminoalkanes (preferably 1,3-diaminopropane) or crosslinked hydroxy- or aminopolystyrene (CLAMPS, commercially available). Suitable polymer enlargers are preferably nucleophiles based on polyethylene glycol or polystyrene. Polyamino acids modified in this way are described in *Chem. Commun.*, 1998, 1159–1160, and *Tetrahedron: Asymmetry*, 1997, 8, 3163–3173.

The amount of the homo-polyamino acid employed is not critical and is normally in the range 0.0001 to 40 mol % (preferably in the range 0.001 to 20 mol %, particularly preferably in the range 0.01 to 15 mol %, and especially in the range 1 to 15 mol %), in each case based on the α,β-unsaturated enone or α,β-unsaturated sulfone employed.

It is also possible to employ the homo-polyamino acids in a form bound to a support, which may be advantageous in relation to the recoverability of the catalyst and the increase in the optical and chemical yield.

For this purpose, the homo-polyamino acids are bound by adsorption to an insoluble support material. The insoluble support materials preferably employed are those based on silica or zeolite, such as, for example, molecular sieves, silica gels, Celite® 521, Celite® Hyflo Super Cell, or Wessalith® DayP. Silica gels with defined pore sizes such as, for example, CPC I or CPC II are also advantageous. Further preferred support materials are activated carbon or sugar derivatives such as, for example, nitrocellulose and cellulose.

The ratio of support material to polyamino acid is given by two limits. On the one hand, only a certain number of polyamino acids can be adsorbed on the insoluble support, and on the other hand, there is a decline in chiral induction with less than 10% by weight of polyamino acid relative to the support onwards. The ratio of homo-polyamino acid to support material is preferably in the range from 1:7 to 2:1 parts by weight, particularly preferably in the range from 1:1 to 1:4 parts by weight.

The method for application to a support is described in detail in EP-A 1,006,127, to which express reference is hereby made. For this purpose, initially a mixture of the appropriate homo-polyamino acid and the support material is suspended in an organic solvent such as an ether (for example THF) and then stirred for a prolonged period, preferably up to 48 hours. The solid is then filtered off and dried.

If such supported catalysts are to be employed, then a particularly suitable device for the epoxidation process is one capable of retaining only the catalyst. This device is preferably an enzyme membrane reactor (C. Wandrey in Enzymes as Catalysts in Organic Synthesis; Ed. M. Schneider, Dordrecht Riedel 1986, 263–284). Preference is likewise given to a simple fixed bed reactor such as, for example, a chromatography column.

The oxidants usually employed are hydrogen peroxide complexes with inorganic carbonates, tertiary amines, amino oxides, amides, phosphanes, or phosphane oxides. The urea/hydrogen peroxide complex has proved particularly suitable.

The amount of the oxidant employed may be varied within the wide limits of 1 to 10 equivalents. Surprisingly, furthermore, short reaction times and high enantiomeric excesses can be achieved even with very small amounts of oxidant in the range 1 to 5 equivalents, preferably 1 to 3 equivalents, and particularly 1 to 2 equivalents.

The process according to the invention is carried out in the presence of a base that may be organic or inorganic. However, organic, non-nucleophilic bases are preferably employed, particularly DBU (1,8-diazabicyclo[5.4.0]undec-7-ene), DBN (1,5-diazabicyclo[4.3.0]non-5-ene), or DABCO (1,4-diazabicyclo[2.2.2]octane).

The amount of the base employed may be varied within the wide limits of 0.1 to 10 equivalents. The reaction according to the invention still takes place with short reaction times and high enantiomeric excesses even with amounts of from 0.5 to 5 equivalents, preferably of from 0.8 to 2 equivalents.

The process according to the invention is carried out using an organic solvent Suitable organic solvents are in general ethers (preferably THF, diethyl ether, or tert-butyl methyl ether), esters (preferably ethyl acetate), amides (preferably dimethylformamide), or sulfoxides (preferably dimethyl sulfoxide).

The temperature used in the epoxidation is generally in the range from −10 to +50° C., preferably in the range from 0 to +40° C., and particularly at +10 to +30° C.

In relation to the procedure for the reaction, normally all the components apart from the base are mixed and then the base is added. However, it is also possible to stir the polyamino acid in the presence of the oxidant, of the base, of the solvent, and of the phase-transfer catalyst for 15 min to 2 hours, and thus preactivate it, and then, without intermediate isolation of the preactivated homo-polyamino acid, to add the substrate to be epoxidized.

The two-phase process according to the invention for the enantio-selective epoxidation of α,β-unsaturated enones and α,β-unsaturated sulfones is distinguished by the possibility of using homo-polyamino acids that have not been preactivated separately. It is possible with this process, because of the presence of a phase-transfer catalyst, to dispense with the normally necessary time-consuming (3 to 5 days) and laborious separate preactivation with intermediate isolation. Substantially higher enantiomeric excesses are usually achieved with the process according to the invention.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The process for preparing polyamino acids often provides catalysts for the Juliá-Colonna epoxidation which vary widely in catalytic activity (*Chirality*, 1997, 9, 198–202). The conversion per unit time and the enantiomeric excess can be compared for a particular substrate only if the same polyamino acid batch is used for the epoxidation reaction. For this reason, direct comparison of new results with results published in the literature is impossible, simply because different catalyst batches are inevitably used. For this reason, a uniform polyleucine batch was used in each of the subsequent examples and comparative examples.

In all the following examples, the conversion and the enantiomeric excess (ee) were determined by methods known from the literature using HPLC on a chiral, nonracemic phase (UV detection).

Examples 1 and 3 and Comparative Examples 2 and 4

Epoxidation of Trans-Chalcone (1) to Epoxychalcone (2) Under Two-Phase and SCAT Conditions Scheme 1:

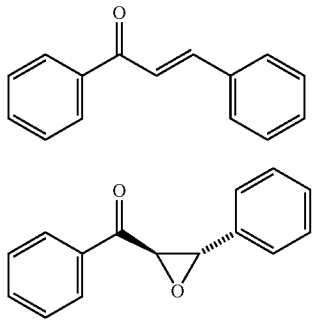

Example 1

2-Phase Conditions with PTC 50 mg of trans-chalcone, 35 mg of urea/hydrogen peroxide complex (UHP, 0.36 mmol, 1.5 equivalents), 8.5 mg of $[(C_4H_9)_4N^+]Br^-$, and 100 mg of pII that had not been separately preactivated (11 mol %) were mixed and, after suspending in 1.5 ml of anhydrous THF, 55 µl of DBU (1.5 equivalents) were added. The reaction mixture was allowed to react at room temperature with stirring. After a reaction time of 30 minutes, the reaction mixture was filtered and the filtrate was concentrated under reduced pressure.

Comparative Example CE 2

2-Phase Conditions Without PTC 50 mg of trans-chalcone, 35 mg of urea/hydrogen peroxide complex (UHP, 0.36 mmol, 1.5 equivalents), and 100 µg of pII that had not been separately preactivated (11 mol %) were mixed and, after suspending with 1.5 ml of anhydrous THF, 55 µl of DBU (1.5 equivalents) were added. The reaction mixture was allowed to react with stirring at room temperature. After a reaction time of 30 min, the reaction mixture was filtered and the filtrate was concentrated under reduced pressure.

Example 3

SCAT Conditions a) Preparation of SCAT 1 g of pII that had not been separately preactivated and 3.4 g of silica gel 60 (230–400 mesh, Merck) were mixed, suspended in 30 ml of anhydrous THF, and stirred slowly for 48 h with exclusion of light. The suspension was filtered and the residue was washed twice with 10 ml of anhydrous THF each time. The material (SCAT) was dried in vacuo over $P_2O_5$.

b) Epoxidation Under SCAT Conditions with PTC 50 mg of trans-chalcone, 35 mg of urea/hydrogen peroxide complex (UHP, 0.36 mmol, 1.5 equivalents), 8.5 mg of $[(C_4H_9)_4N^+]Br^-$, and 100 mg of SCAT (11 mol %) were mixed and, after suspending with 1.5 ml of anhydrous THF, 55 µl of DBU (1.5 equivalents) were added. The reaction mixture was allowed to react with stirring at room temperature. After a reaction time of 30 min, the reaction mixture was filtered and concentrated under reduced pressure.

Comparative Example CE 4

SCAT Conditions Without PTC a) Preparation of SCAT 1 g of non-separately preactivated pII and 3.4 g of silica gel 60 (230–400 mesh, Merck) were mixed, suspended in 30 ml of anhydrous THF, and stirred slowly for 48 h with exclusion of light. The suspension was filtered and the residue was washed twice with 10 ml of anhydrous THF each time. The material (SCAT) was dried in vacuo over $P_2O_5$.

b) Epoxidation Under SCAT Conditions Without PTC 50 mg of trans-chalcone, 35 mg of urea/hydrogen peroxide complex (UHP, 0.36 mmol, 1.5 equivalents), and 100 mg of SCAT (11 mol %) were mixed and, after suspending with 1.5 ml of anhydrous THF, 55 µl of DBU (1.5 equivalents) were added. The reaction mixture was allowed to react with stirring at room temperature. After a reaction time of 30 min, the reaction mixture was filtered and concentrated under reduced pressure.

The results of Examples 1 and 3 and of Comparative Examples CE 2 and 4 are compiled in the table below.

TABLE

| Example | Conditions | PTC | Reaction time [min] | Conversion [%] | ee [%] |
|---|---|---|---|---|---|
| 1 | according to the invention | $[(C_4H_9)_4N^+]Br^-$ | 30 | >99 | 78 |
| CE 2 | 2-phase; not according to the invention | — | 30 | >99 | 53 |
| 3 | according to the invention | $[(C_4H_9)_4N^+]Br^-$ | 30 | >99 | 92 |
| CE 4 | 2-phase, SCAT; not according to the invention | — | 30 | >99 | 86 |

What is claimed is:

1. A process comprising epoxidizing at least one α,β-unsaturated sulfone or at least one α,β-unsaturated sulfone in the presence of
   (1) an organic solvent,
   (2) a base,
   (3) an oxidant,
   (4) a diastereomer- and enantiomer-enriched homo-polyamino acid as a catalyst that has not been separately preactivated, and
   (5) a phase-transfer catalyst, without addition of water, wherein the homo-polyamino acid is applied by adsorption to an insoluble support material.

2. A process according to claim 1 wherein the insoluble support material is based on a material selected from the group consisting of silica, zeolite, activated carbon, sugar derivatives, and combinations thereof.

* * * * *